(12) United States Patent
Lueck et al.

(10) Patent No.: US 7,855,081 B2
(45) Date of Patent: Dec. 21, 2010

(54) METHODS OF DETECTING RF INTERFERENCE IN BREATH ETHANOL TESTING

(75) Inventors: Keith W. Lueck, Fenton, MO (US); M. Rankine Forrester, St. Louis, MO (US); Gary L. Sibley, St. Louis, MO (US); John Mitchell, Manchester, MO (US)

(73) Assignees: Intoximeters, Inc., St. Louis, MO (US); Alcotek, Inc., St. Louis, MO (US)

( * ) Notice: Subject to any disclaimer, the term of this patent is extended or adjusted under 35 U.S.C. 154(b) by 301 days.

(21) Appl. No.: 11/872,541

(22) Filed: Oct. 15, 2007

(65) Prior Publication Data

US 2008/0030357 A1 Feb. 7, 2008

Related U.S. Application Data

(62) Division of application No. 10/891,817, filed on Jul. 15, 2004.

(60) Provisional application No. 60/504,925, filed on Sep. 22, 2003.

(51) Int. Cl.
*G01N 1/22* (2006.01)

(52) U.S. Cl. .................. 436/132; 436/900; 422/84; 73/23.3; 600/532

(58) Field of Classification Search .................. 436/132, 436/900; 422/84; 73/23.3; 600/532
See application file for complete search history.

(56) References Cited

U.S. PATENT DOCUMENTS

| | | | |
|---|---|---|---|
| 3,792,272 A | 2/1974 | Harte et al. | |
| 4,163,383 A | 8/1979 | VanderSyde et al. | |
| 4,407,152 A | 10/1983 | Guth | |
| 4,487,055 A | 12/1984 | Wolf | |
| 4,671,298 A | 6/1987 | Babb et al. | |
| 4,770,026 A | 9/1988 | Wolf | |
| 4,996,161 A | 2/1991 | Conners et al. | |
| 5,180,513 A | 1/1993 | Durand | |
| 5,255,656 A | 10/1993 | Rader et al. | |
| 5,393,495 A | 2/1995 | Forrester | |
| 5,400,758 A | 3/1995 | Rader et al. | |
| 5,408,330 A | 4/1995 | Squicciarini et al. | |
| 5,498,985 A | 3/1996 | Parle et al. | |
| 6,075,444 A | 6/2000 | Sohege et al. | |

(Continued)

FOREIGN PATENT DOCUMENTS

WO 02079769 A2 10/2002

OTHER PUBLICATIONS

International Search Report dated Jul. 27, 2006, Application No. PCT/US2004/30851, 7 Pages.

(Continued)

*Primary Examiner*—Lyle A Alexander
(74) *Attorney, Agent, or Firm*—Armstrong Teasdale LLP

(57) ABSTRACT

Interference detector and methods for detecting interference in a signal are described. More specifically, in one aspect, a method for detecting interference in a signal is provided. The method comprises determining whether the signal has at least one of a time and a frequency characteristic that is outside a predefined range, and determining that an interference event has been detected if the signal has at least one of such characteristics.

14 Claims, 6 Drawing Sheets

U.S. PATENT DOCUMENTS

| | | |
|---|---|---|
| 6,096,558 A | 8/2000 | Stock |
| 6,129,894 A | 10/2000 | Rabenecker et al. |
| 6,150,177 A | 11/2000 | Stock |
| 6,289,718 B1 | 9/2001 | Stock |
| 6,348,355 B1 | 2/2002 | Bather et al. |
| 6,464,941 B1 | 10/2002 | Diekmann |
| 6,564,084 B2 | 5/2003 | Allred, III et al. |
| 6,598,459 B1 | 7/2003 | Fu |
| 6,735,477 B2 | 5/2004 | Levine |
| 7,221,312 B2 * | 5/2007 | Yee et al. ............... 342/357.02 |
| 2004/0089055 A1 | 5/2004 | Cramer et al. |

OTHER PUBLICATIONS

European Search Report mailed Feb. 18, 2010 re PCT/US2004/030851; 5 pages.

* cited by examiner

F I G . 3
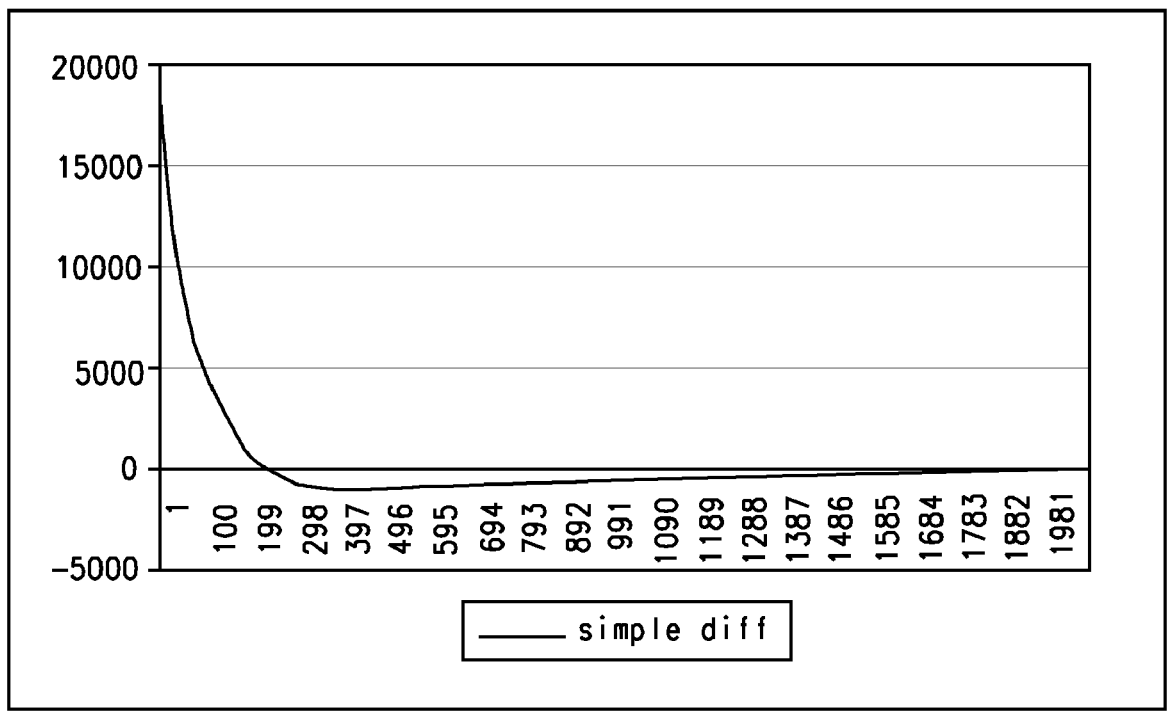
F I G . 4

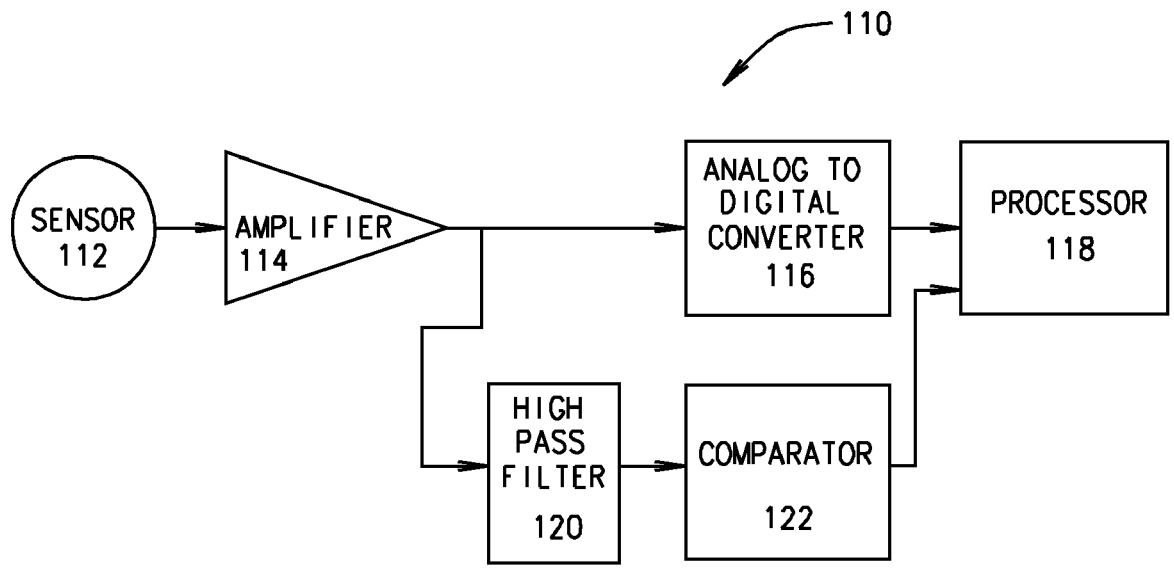
F I G . 1 1
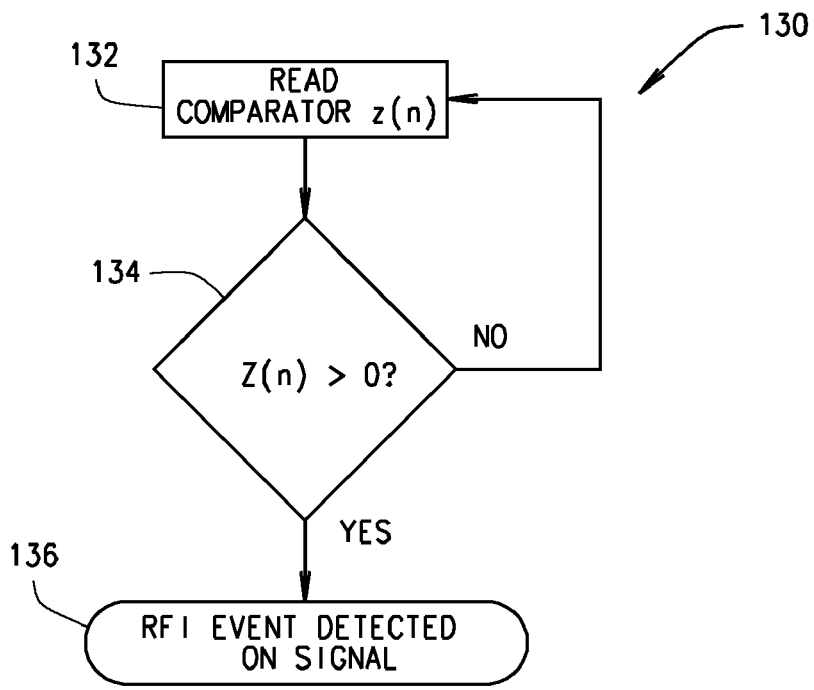
F I G . 1 2

METHODS OF DETECTING RF INTERFERENCE IN BREATH ETHANOL TESTING

CROSS REFERENCE TO RELATED APPLICATIONS

This application is a divisional of U.S. patent application Ser. No. 10/891,817, filed Jul. 15, 2004, which is hereby incorporated by reference in its entirety and is assigned to the same assignee. U.S. patent application Ser. No. 10/891,817 claims the benefit of U.S. Provisional Application Ser. No. 60/504,925 filed on Sep. 22, 2003.

BACKGROUND OF THE INVENTION

This invention relates generally to detecting electro-magnetic interference and more particularly, to electro-magnetic interference detection systems and methods for instruments such as breath testers.

Breath testing instruments often times are operated in the presence of devices that may emit electro-magnetic signals such as radio frequency (RF) signals. For example, police radios and controls for police video recorders, emit such signals. Electro-magnetic signals can interfere with the operation of a breath testing instrument, and accordingly, such instruments therefore should be substantially, if not totally, immune to electro-magnetic interference (EMI). EMI refers to an electro-magnetic signal or wave, radiated or conducted, from any source that interferes with normal operation of a device.

EMI detection circuits are sometimes utilized in connection with breath testing instruments. Such EMI detection circuits, however, typically operate only over a certain frequency band that includes the frequency range of police radios. Since police radios are likely to be present at the site of a breath testing device, detecting EMI within such frequency band is beneficial. EMI can, however, be generated from numerous sources at various frequencies and field strengths that may have little to do with a police radio.

In addition, with some known EMI detectors, an antenna and sensor are used to detect interference. Designing an antenna and sensor system across a broad band of frequencies and equally sensitive at all frequencies is highly complex. Further, the circuit and circuit components at risk for EMI may present different responses to different frequencies and therefore, the response of the detector circuit should be matched to the response of the circuit at risk, which further increases complexity. Also, a detector circuit that is separate from the circuit at risk is necessarily located in a different physical location than the circuit at risk. Therefore, there is less than absolute certainty that the detector circuit is "seeing" the same exposure to EMI as the circuit at risk. The complexity and uncertainty associated with such systems may result in possibilities for a false alarm or no alarm when interference is present.

In addition to, or rather than, an EMI detection circuit, shielding can be employed to shield at least certain components of the instrument, or the entire instrument, from EMI. While shielding is effective to at least some extent, such shielding is generally only effective up to a defined level of interference. At interference levels above such predefined level, there is a risk of interference impacting the integrity of the system. Also, over time, there is a possibility for shielding to become compromised through physical decay, corrosion, improper service, and other factors. Ensuring EMI immunity over the life of an instrument based on such shielding generally is not possible.

BRIEF SUMMARY OF THE INVENTION

In one aspect, a method for detecting interference in a signal comprises receiving a sample signal. The signal is compared to a predetermined expected sensor signal range including at least one of a predetermined time rate of change range and a predetermined frequency range by comparing the signal to a predefined threshold. The method also includes determining whether the signal has at least one of a time and a frequency characteristic outside a predefined range, and determining that an interference event has been detected if the signal has at least one of such characteristics.

In another aspect, an interference detector for detecting electro-magnetic interference in a signal is provided. The detector includes a processor programmed to process a signal representative of breath alcohol content to determine whether the signal has been corrupted by electro-magnetic interference, and to determine whether the signal has at least one of a time characteristic and a frequency characteristic outside respective predefined ranges.

BRIEF DESCRIPTION OF THE DRAWINGS

FIG. 3 is an exemplary graph illustrating a waveform generated by a fuel cell in a breath alcohol test instrument.

FIG. 4 is an exemplary graph illustrating a signal generated by differentiating the signal shown in FIG. 3.

FIG. 11 is a block diagram of yet another embodiment of a breath testing instrument.

FIG. 12 is a flow chart illustrating a exemplary method for detecting EMI in the instrument illustrated in FIG. 11.

DETAILED DESCRIPTION OF THE INVENTION

The methods and systems described herein generally are directed to detecting the presence of radio frequency signals that may adversely impact desired operation of a breath testing instrument. Such methods and systems can be used in combination with other interference reduction/elimination techniques (e.g., shielding), and are not limited to practice in only breath testing devices. For example, such methods and systems can be utilized in connection with any device wherein interference is desired to be detected.

Generally, once interference is detected, many different approaches can be taken with respect to the signal that may be corrupted by the interference. For example, the signal can be discarded or ignored.

Figure 1:
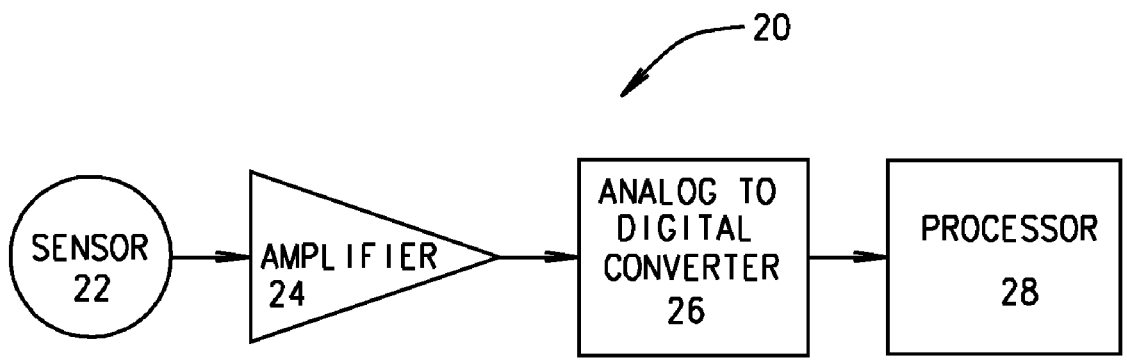
FIG. 1 is a block diagram of an exemplary embodiment of a breath testing instrument.

Referring specifically to the drawings, FIG. 1 is a block diagram of an exemplary breath testing instrument 20. Breath testing instrument 20 includes a sensor 22. Sensor 22 can be in one of many forms. In one example, sensor 22 is a fuel cell. Fuel cells are commonly employed in breath testing instruments.

An output of fuel cell 22 is coupled to an amplifier 24. In an example embodiment, amplifier 24 is an operational amplifier (op-amp) coupled to the output of sensor 22.

An output of amplifier 24 is coupled to an analog-to-digital converter 26. Converter 26 converts an analog output signal from amplifier 24 into a digital signal. An output of converter 26 is coupled to a processor 28. Processor 28 executes an alcohol detection algorithm on the digital signal from converter 26, and generates a display signal that is then displayed to an operator of instrument 20.

The term "sensor", as used herein, refers to any device that generates a signal representative of a quantity or quality to be measured or monitored, quantitatively or qualitatively. In the context of breath alcohol, for example, the term sensor refers to a device that generates a signal representative of breath alcohol content. Examples of such sensors include electrochemical fuel cell, semiconductor, infrared, gas chromatograph, and mass spectrometer sensors.

The term "processor", as used herein, is not limited to reference a microprocessor. Rather, the term "processor" is used to refer to any device or group of devices capable of processing the signal from the sensor (in analog or digital form) for the purpose of determining whether such signal has been corrupted by interference. For example, in addition to a microprocessor, it is contemplated that digital signal processors, analog processors, analog devices (e.g., switched capacitors), analog/digital logic circuits, discrete transistors, integrated circuits, and many other devices can be used to perform such processing. The term "processor", as used herein, includes all such devices. In addition, it is contemplated that a sensor and a processor can be implemented in one circuit, for example, in the form of an integrated circuit.

The term "interference", as used herein, refers to an interruption of, or interference with, proper operation of a device. For example, in the context of a breath alcohol sensor, the sensor may generate a signal that has been interfered with due to EMI. Corruption of the signal by EMI is referred to herein as interference. In comparison to corruption of the signal by EMI, interferents may be present in the sample provided to the tester. For example, in the context of a breath alcohol sensor, the presence of mouth alcohol will result in the sensor generating a signal that may not be fully representative of breath alcohol from the deep lung. In such a circumstance, the device operates properly yet the measurement generated by the device may not be accurate with respect to the desired deep lung breath alcohol concentration. Such inaccuracy is not caused by interference. Rather, the sample used by the properly operating device is not a valid sample.

FIG. 1 is just one example breath testing instrument, and many different configurations and components can be used in performing breath testing. Further details regarding breath testing instruments are set forth, for example, in U.S. Pat. Nos. 5,393,495 and 4,770,026.

As explained above, electro-magnetic interference (EMI) can impact the integrity of a signal generated by sensor 22, or can possibly even impact operation of amplifier 24 and/or converter 26. Especially in devices such as a breath testing instrument, there are many reasons for maintaining the integrity of the signal and operation of the instrument components.

Generally, to detect interference, deviations or abnormalities from an expected sensor signal are detected. As explained below in detail, the expected sensor signal has a well defined bandwidth and wave shape. If the bandwidth or wave shape deviates outside the expected, or normal, range by extending beyond the pre-defined upper or lower thresholds, then interference has likely corrupted the signal. The range, including the upper and lower thresholds, can be determined empirically and depends on the particular sensor and associated circuitry employed.

Figure 2:
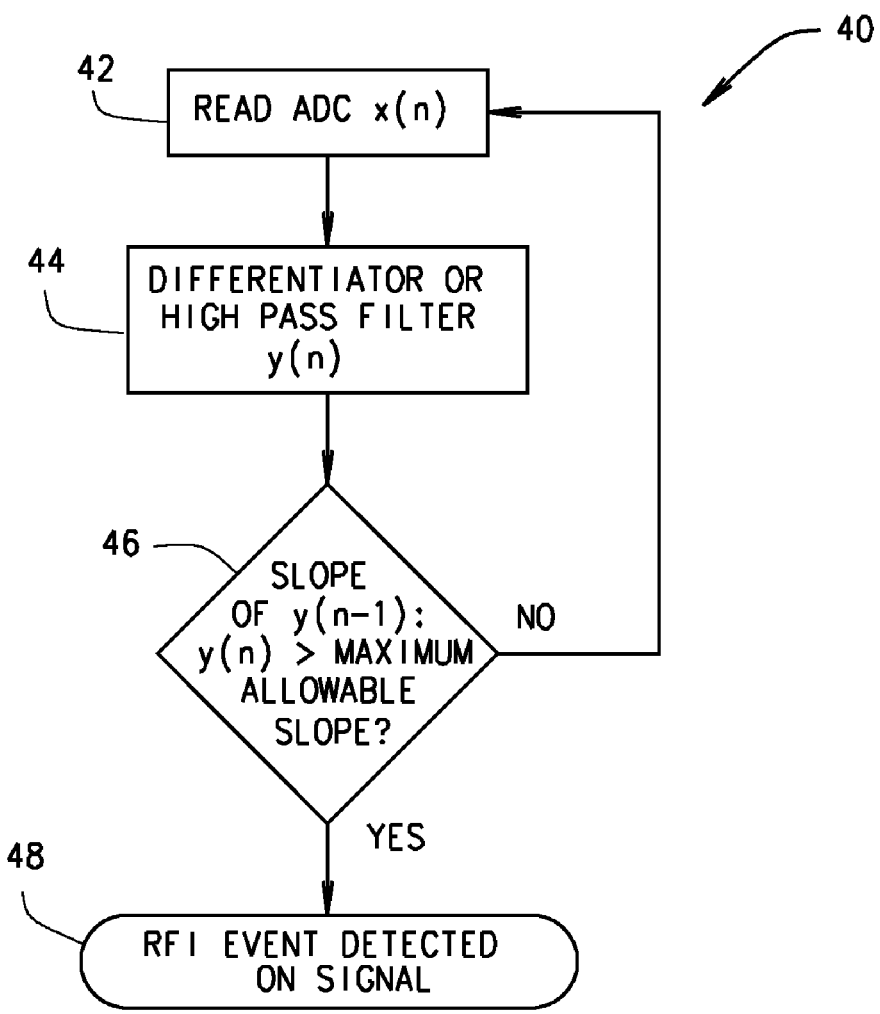
FIG. 2 is a flow chart illustrating an exemplary method for detecting EMI in the instrument illustrated in FIG. 1.

In accordance with one embodiment, and in addition to executing an alcohol detection algorithm, processor 28 is programmed to perform an interference detection algorithm. An example embodiment of such an algorithm 40 is shown in FIG. 2. Referring to FIG. 2, processor 28 reads or samples 42 a digital signal ($x(n)$) at the output of converter 26. The signal is then differentiated, or high-pass filtered, 44 to generate a differentiated, or filtered, signal $y(n)$. The slope of the signal ($y(n)$) is then compared 46 to a predetermined maximum allowable slope, i.e., a predefined threshold. Generally, if the determined slope is within a predefined range, i.e., within the defined lower and upper limits, or thresholds, of the range, then processing returns to sampling 42 the signal at the output of converter 26. However, if the determined signal slope is greater than the maximum allowable slope, for example, then an interference event is detected 48.

In the exemplary embodiment, upon detection of an interference event, the sampled signal ($x(n)$) is discarded and further processing is not performed using such signal. If no interference event is detected, then the sampled signal ($x(n)$) is utilized in connection with respect to generating a signal representative of breath alcohol content.

With respect to sensor 22, there are many sensors (such as fuel cells, for example) that generate outputs having well defined bandwidths or wave shapes. To detect interference, high-pass filtering is performed on the generated signal, and deviations from pre-defined limits are identified. Interference can manifest as DC offsets, and low-pass filtering may merely "smear" the interference energy and corrupt the data contained in the signal. Therefore, although low pass filtering can be used, high-pass filtering separates the components of the interference from the data leaving only the components of the interference if interference is present.

More particularly, since the bandwidth of the signal generated by sensor 22 is well defined, a filter may be configured to remove the data from the signal, leaving the interference. Since certain characteristics of the signal are known, such as its slope, or even the mathematical sign of its slope, simpler techniques such as differentiation can be used. Higher order derivatives (e.g., the slope of the slope) of the signal could also be used.

The filter can have many forms and can be implemented in hardware or software. The high-pass filtering can be performed using known frequency- or time-domain techniques in hardware or software. The filtering can be executed in real-time, or after the fact on stored data. Hardware-based filtering can be performed using, for example, switched-capacitor or analog techniques. Software-based filtering can be performed using, for example, time-domain techniques such as FIR/IIR filtering or differentiation. Fourier Transform and other frequency-based techniques also can be used.

In operation, and with a fuel cell as sensor 22, a waveform generated by fuel cell in breath alcohol testing has a well-defined shape, such as shown in FIG. 3. The signal rises, peaks, and then decays. An uncorrupted waveform has a positive slope gradually changing to zero, and then becoming negative. Differentiating such a signal yields a signal, such as is shown in FIG. 4.

With the signal shown in FIG. 3, there should be no negative slope before the peak, nor a positive slope after the peak. That is, the derivative of the signal (FIG. 4) should tend monotonically toward a negative value, then monotonically rebound toward zero. Any deviation from this profile indicates possible interference.

Figure 5:
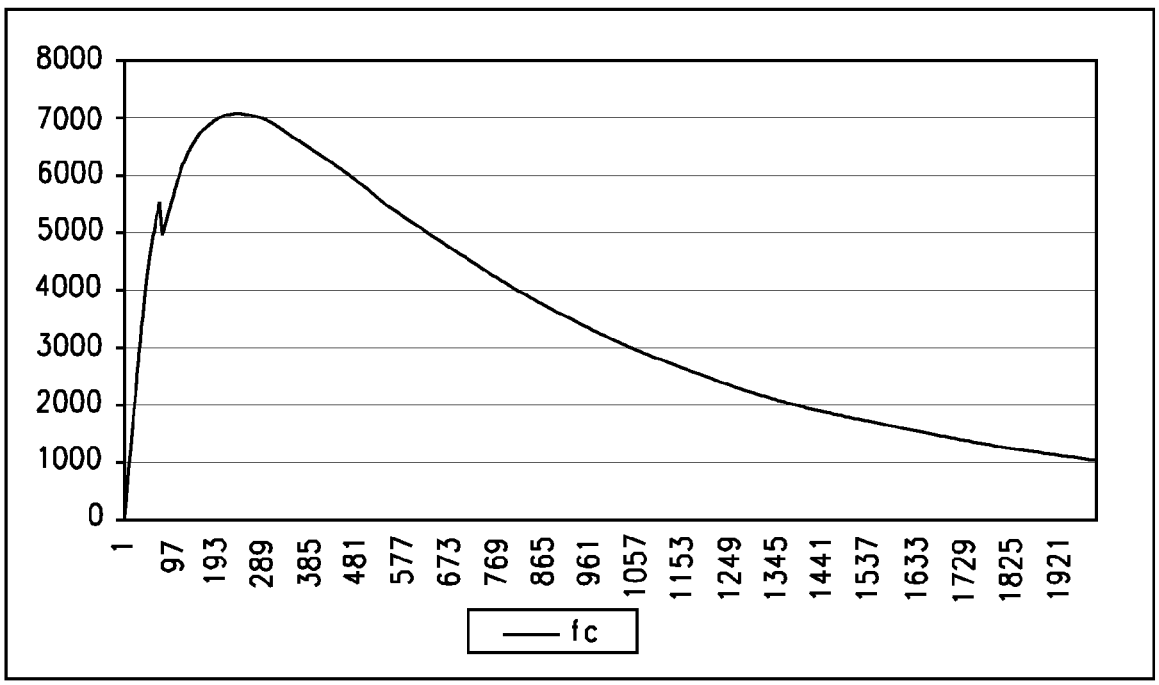
FIG. 5 is an exemplary graph illustrating a waveform having a small positive offset on its rising edge.
Figure 6:
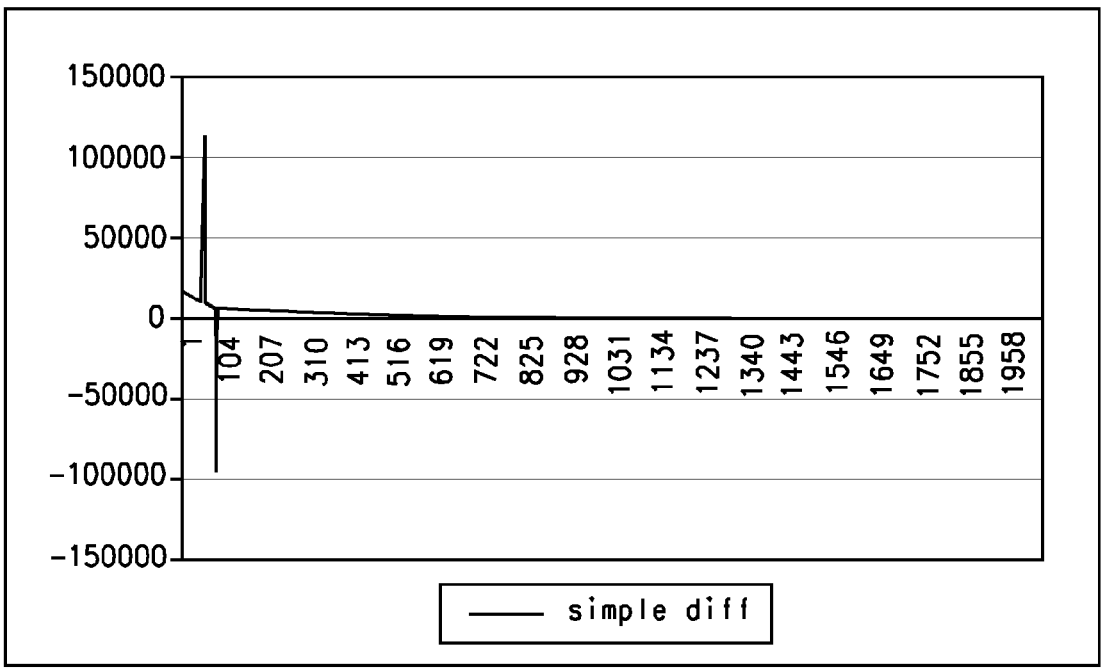
FIG. 6 is an exemplary graph illustrating a signal generated by differentiating the signal shown in FIG. 5.

For example, and referring to FIG. 5, the signal has a small positive offset on its rising edge. Differentiating this signal yields the signal shown in FIG. 6. The interference is clear due to the spikes extending upward and downward. The normal or expected (i.e., uncorrupted) slope of the signal in FIG. 5 at this point in time is below some positive range and should not be negative.

Figure 7:
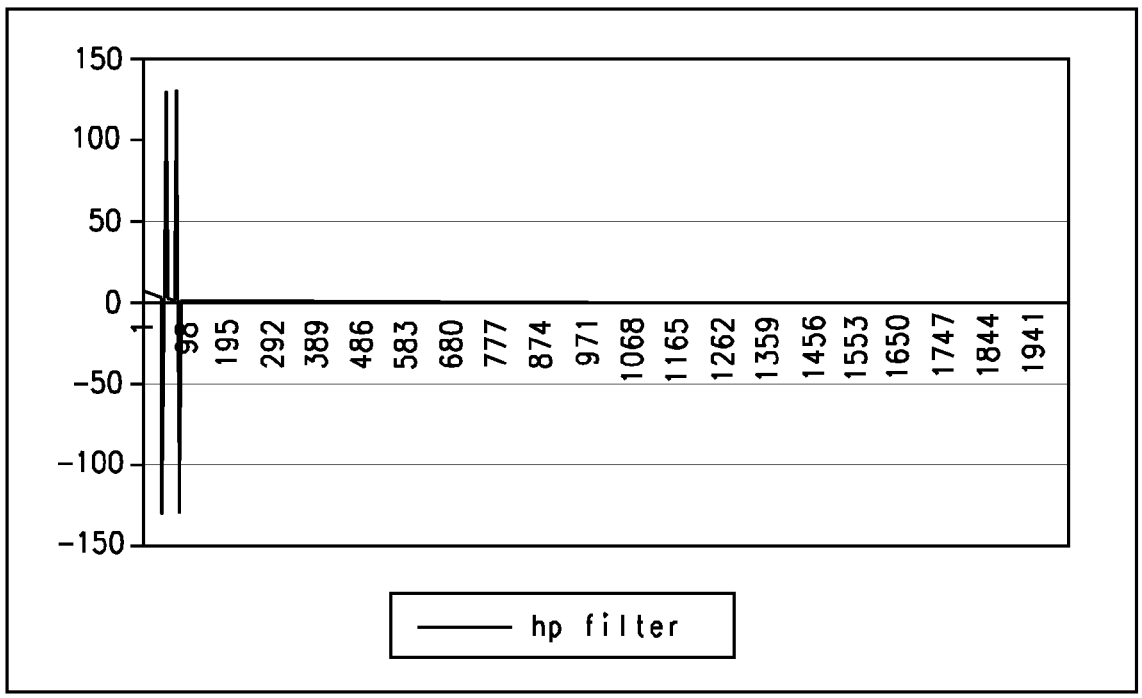
FIG. 7 is an exemplary graph illustrating the signal resulting from high-pass filtering the signal shown in FIG. 5.

Similarly, if a high-pass filter is applied to the signal shown in FIG. 5, then the signal shown in FIG. 7 is generated. As with differentiation, the presence of the interference is clear once the signal is high-pass filtered.

The above-described system and method provide the advantage that the circuit at risk of interference is itself used as the detector. Therefore, issues associated with frequency matching and physical placement between detection and the circuit at risk are eliminated. In addition, if ancillary shielding or grounding becomes ineffective for any reason, the above-described system and method still safeguard the integrity of the signal and the data derived from the signal. The above-described system and method therefore facilitate minimizing the risks of (1) generating no alarm when there is interference and (2) generating a false alarm when interference does not exist.

Figure 8:
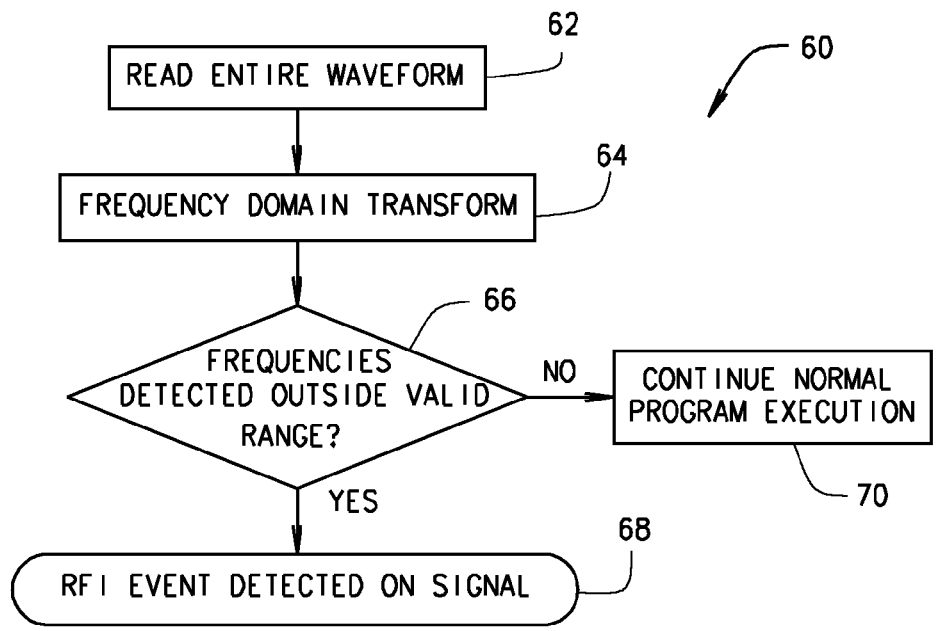
FIG. 8 is a flow chart illustrating an alternative method for detecting EMI in the instrument illustrated in FIG. 1.

FIG. 8 is a flow chart illustrating another embodiment of a method for detecting interference in an instrument, such as instrument 20 (shown in FIG. 1). Referring specifically to FIG. 8, an entire waveform is read 62 by processor 28. The waveform is then transformed 64 to the frequency domain by processor 28. Processor 28 then determines whether any components of the transformed signal have frequencies outside a predefined, or valid, range 66. If there are signals outside the valid range, i.e., signals that exceed a predefined threshold, then an interference event is deemed detected 68. As explained above, once interference is detected, many different approaches can be taken with respect to the signal that may be impacted by the interference. For example, the signal can be discarded or ignored. If there are no frequency components outside the valid range, then normal program processing is executed on the waveform 70.

Figure 9:
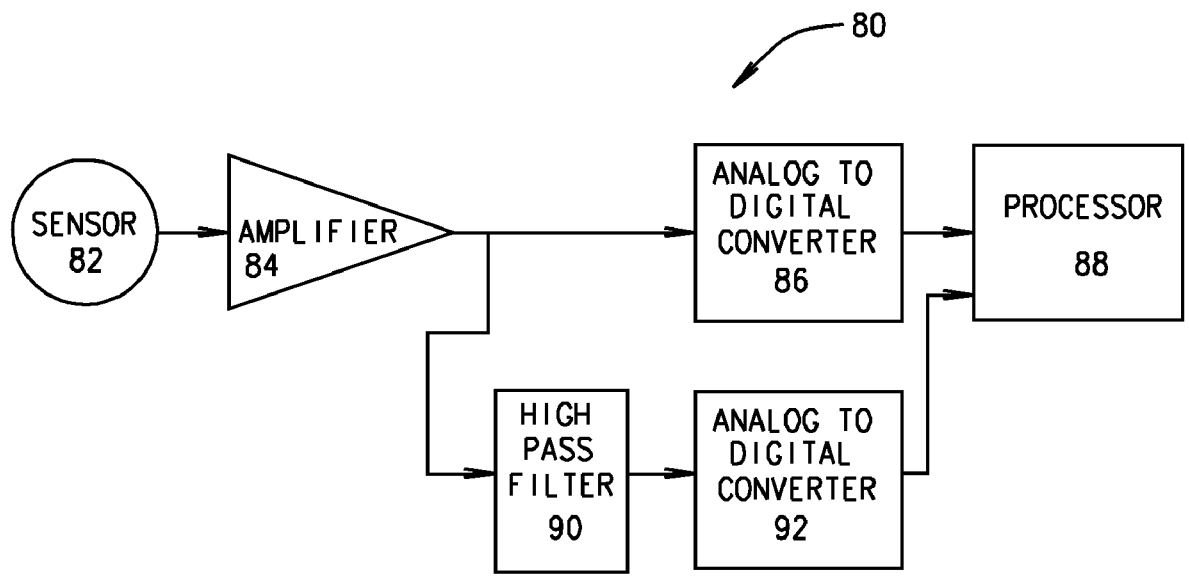
FIG. 9 is a block diagram of an alternative embodiment of a breath testing instrument.

FIG. 9 is a block diagram of another embodiment of a breath testing instrument 80. Breath testing instrument 80 includes a sensor 82. Sensor 82 can be in one of many forms. In the exemplary embodiment, sensor 82 is a fuel cell. An output of fuel cell 82 is coupled to an amplifier 84. In the exemplary embodiment, amplifier 84 is an operational amplifier (op-amp) coupled to the output of sensor 82. An output of amplifier 84 is coupled to a first analog-to-digital converter 86. Converter 86 converts an analog output signal from amplifier 84 into a digital signal. An output of converter 86 is coupled to a processor 88. Processor 88 executes an alcohol detection algorithm on the digital signal received from converter 86, and generates a display signal that is then displayed to an operator of instrument 80.

The output of amplifier 84 is also coupled to a high-pass filter 90 and to a second analog to digital converter 92 that is connected in parallel with respect to first converter 86. Processor 88 therefore samples two digital signals, i.e., a signal from first converter 86 and a filtered signal from second converter 92. The signal from first converter 86 is temporarily stored by processor 88 while operations are executed on the filtered digital signal to determine whether an interference event has occurred. If an interference event is detected, then the signal from first converter 86 is discarded. If no interference event is detected, then further processing is performed on the signal from first converter 86.

Figure 10:
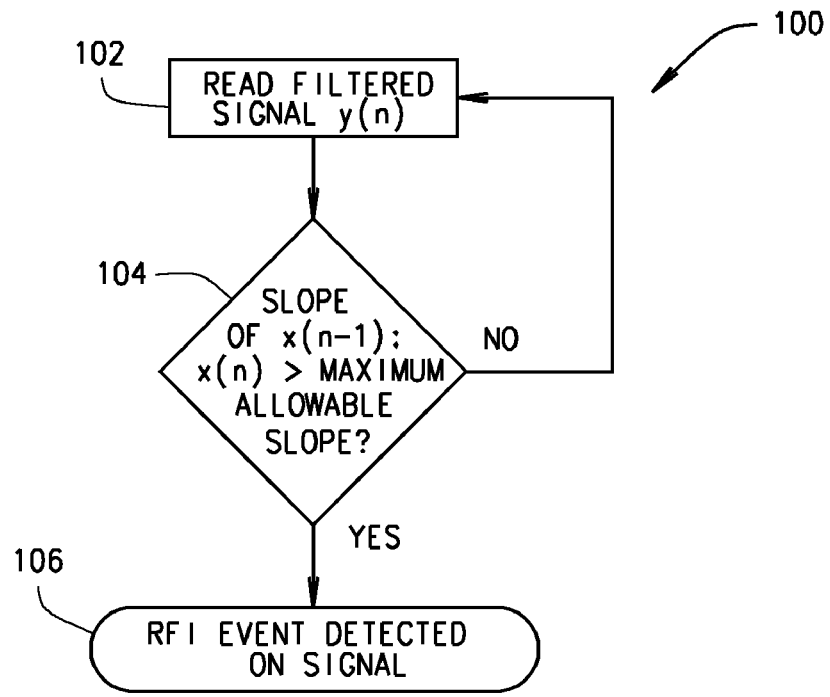
FIG. 10 is a flow chart illustrating an exemplary method for detecting EMI in the instrument illustrated in FIG. 9.

With respect to a process 100 for determining whether an interference event has occurred, and referring to FIG. 10, processor 88 reads 102 a filtered digital signal (y(n)) at the output of converter 92, which estimates the slope of this signal x(n). The slope of the signal (y(n)) is then compared 104 to a predetermined maximum allowable slope. If the signal slope is less than or equal to the maximum allowable slope, i.e., a predefined threshold, then processing returns to sampling 102 the signal at the output of converter 92. If, however, the signal slope is greater than the maximum allowable slope, then an interference event is detected 106. As explained above, higher order derivatives (i.e., the slope of the slope) could be used.

In the example embodiment, and upon detection of an interference event, the sampled signal (x(n)) from first converter 86 is discarded and further processing is not performed using such a signal. If, however, no interference event is detected, then the sampled signal (x(n)) is utilized in connection with respect to generating a signal representative of breath alcohol content.

FIG. 11 is a block diagram of yet another embodiment of a breath testing instrument 110. Breath testing instrument 110 includes a sensor 112. Sensor 112 can be in one of many forms. In the exemplary embodiment, sensor 112 is a fuel cell. An output of sensor 112 is coupled to an amplifier 114. In the exemplary embodiment, amplifier 114 is an operational amplifier (op-amp) that is coupled to the output of sensor 112.

An output of amplifier 114 is coupled to an analog-to-digital converter 116. Converter 116 converts an analog output signal from amplifier 114 into a digital signal. An output of converter 116 is coupled to a processor 118. Processor 118 executes an alcohol detection algorithm on the digital signal received from converter 116, and generates a display signal that is then displayed to an operator of instrument 110.

The output of amplifier 114 also is coupled to a high-pass filter 120 and a comparator 122 that is connected in parallel with respect to first analog to digital converter 116. Processor 118 therefore samples two signals, i.e., a signal from first converter 116 and a filtered signal from comparator 122. If an interference event is detected, then the signal from first converter 116 is discarded or ignored. If, however, no interference event is detected, then further processing is performed on the signal from first converter 116.

FIG. 12 is a flow chart illustrating an embodiment of a method 130 for detecting interference in instrument 110 illustrated in FIG. 11. Referring to FIG. 12, comparator 122 compares the signal from high-pass filter 120 to a predetermined maximum allowable signal, i.e., a predefined threshold. Processor 118 reads 132 a signal (x(n)) at the output of comparator 122. If the signal from comparator 122 is less than or equal to zero 134, then processing returns to reading 132 the signal at the output of comparator 122. If, however, the signal from comparator 122 is greater than zero, then an interference event is detected 136.

In the exemplary embodiment, and upon detection of an interference event, the sampled signal (x(n)) from converter 116 is discarded and further processing is not performed using such signal. However, if no interference event is detected, then the sampled signal (x(n)) is utilized in connection with respect to generating a signal representative of breath alcohol content.

The above-described systems and methods provide the advantage of using the signal itself from a circuit at risk to detect interference that may damage signal integrity. Generally, and as described above, such systems and methods can be utilized when a signal without interference has a well-defined time, or frequency characteristic. If a signal that should have such a well defined time or frequency characteristic does not have such defined characteristics, then an interference event is deemed detected. Specifically, the signal is processed so that only possible interference remains. By evaluating the remaining interference, it can be determined whether the data from the circuit-at-risk can be relied upon or whether it should be discarded. Thus, the interference data from the circuit-at-risk is used in connection with detecting interference.

The above-described systems and methods can be used in connection with many different circuits at risk, and the circuits described above are by way of example only. In addition, there can be multiple detectors for multiple circuits, and detectors may be chosen only for those circuits and signals most likely to be at risk. Detectors and circuits may be tied to multiple signals, each of which could be thus protected. Moreover, single signals may be tied to multiple circuits and detectors. For example, multiple interference detection algorithms can be executed in connection with one signal to determine the existence of interference.

In addition, the above-described systems and methods can be accomplished through frequency- and/or time-domain techniques in hardware and/or software. The detection algorithms can be executed in real-time, or not in real-time on stored data. Rather than executing algorithms implemented in software, hardware detection methods can be used, including switched-capacitor or analog technology. Of course, other hardware detection methods could be used. In addition, with respect to detection algorithms implemented in software, time domain techniques such as digital filtering, differentiation (of any order), or a variety of other frequency-based techniques such as the FFT (fast Fourier transform) can be used. Again, other software methods could be used.

Although a few specific types of breath tester are described herein, the above-described methods and system can be used on other types of breath tester signals and other circuits at risk, such as, but not limited to, ethanol and/or $CO_2$ infrared signals from a breath test, instrument temperature data, absolute and gauge pressure for use with dry gas standards, breath flow, mechanism position sensing, and any other signal in a breath tester with well defined time or frequency characteristics.

While the invention has been described in terms of various specific embodiments, those skilled in the art will recognize that the invention can be practiced with modification within the spirit and scope of the claims.

What is claimed is:

1. A method for detecting electro-magnetic interference corrupting a signal from a breath alcohol sensor, said method comprising:
   receiving the signal from the breath alcohol sensor;
   differentiating the signal to generate a differentiated signal;
   comparing the differentiated signal to a predefined threshold for a time rate of change range; and
   determining that an interference corrupting event is detected if the time rate of change is outside the respective predetermined range.

2. A method for detecting electro-magnetic interference corrupting a signal received from a breath alcohol sensor including a fuel cell, the method comprising:
   receiving the signal from the breath alcohol sensor;
   transforming the signal from a time domain signal to a frequency domain signal; and
   processing the frequency domain signal to determine whether any frequency component present is outside a predefined range; and
   determining that an interference corrupting event is detected if the frequency component present is outside the predefined range.

3. A method in accordance with claim 1 further comprising discarding the signal if the interference corrupting event is detected.

4. A method in accordance with claim 1 further comprising determining a second order or higher order derivative of the signal.

5. A method in accordance with claim 1 further comprising converting the signal into a digital signal.

6. The method of claim 1 wherein the differentiated signal has a slope and wherein the comparing step includes comparing the slope of the differentiated signal to a maximum allowable slope.

7. The method of claim 6 wherein the interference corrupting event is detected if the slope is greater than the maximum allowable slope.

8. The method of claim 7 further comprising discarding the signal if the interference corrupting event is detected.

9. A method in accordance with claim 2 further comprising discarding the signal if the interference corrupting event is detected.

10. A method in accordance with claim 2 further comprising determining a second order or higher order derivative of the signal.

11. A method in accordance with claim 2 further comprising converting the signal into a digital signal.

12. The method of claim 2 wherein the frequency domain signal has a slope and wherein the comparing step includes comparing the slope of the signal to a maximum allowable slope.

13. The method of claim 12 wherein an interference event is detected if the slope is greater than the maximum allowable slope.

14. The method of claim 13 further comprising discarding the signal if the interference event is detected.

* * * * *